(12) United States Patent
Heggie et al.

(10) Patent No.: US 6,177,560 B1
(45) Date of Patent: Jan. 23, 2001

(54) PROCESS FOR THE PREPARATION OF MOMETASONE FUROATE

(75) Inventors: William Heggie, Palmela; Joao Bandarra, Loures, both of (PT)

(73) Assignee: Hovione Inter Ltd. (CH)

( * ) Notice: Under 35 U.S.C. 154(b), the term of this patent shall be extended for 0 days.

(21) Appl. No.: 09/476,004

(22) Filed: Dec. 29, 1999

(30) Foreign Application Priority Data

Aug. 2, 1999 (PT) ....................................................... 102343

(51) Int. Cl.⁷ ....................................................... C07J 17/00
(52) U.S. Cl. .......................... 540/116; 540/114; 540/119; 540/116
(58) Field of Search ..................... 540/116, 119

(56) References Cited

U.S. PATENT DOCUMENTS 4,472,393   9/1984   Shapiro .
5,886,200 * 3/1999   Kwok et al. ......................... 552/577

FOREIGN PATENT DOCUMENTS

9800437 * 1/1998 (WO) ............................... C07J/7/00

OTHER PUBLICATIONS

Draper et al. (Ca 130:325286, abstract of Tetrahederon (1999), 55(11), 3355–3364, 1999.*

* cited by examiner

Primary Examiner—Jose' G. Dees
Assistant Examiner—Sabiha Qazi
(74) Attorney, Agent, or Firm—Ostrolenk, Faber, Gerb & Soffen, LLP

(57) ABSTRACT

The invention provides a new process for the preparation of mometasone 17-furoate, a steroid derivative useful in the treatment of inflammatory disease, by direct esterification of the 17 hydroxyl group without prior protection of the free 11 hydroxy function.

8 Claims, No Drawings

PROCESS FOR THE PREPARATION OF MOMETASONE FUROATE

Mometasone furoate is a well known (Shapiro and Grove, U.S. Pat. No. 4,472,393 and Kwok, Tsi, Tan and Fu; WO98/00437) and potent anti-inflammatory steroid having the structure:

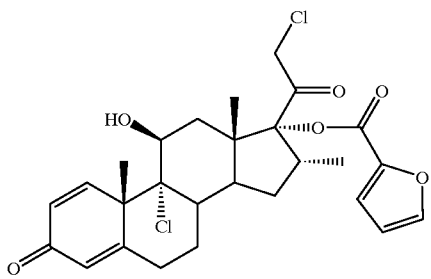

U.S. Pat. No. 4,472,393 describes two processes for the production of mometasone furoate. In Example 12, Method I uses 9β,11β-epoxy-17α,21-dihydroxy-16α-methyl-1,4-pregnadien-3,20-dione as a starting material, whereas Method II uses 21-chloro-17α-hydroxy-16α-methyl-1,4,9(11)-pregnatriene-3,20-dione. WO98/00437 describes an improved process from 9β,11β-epoxy-17α,21-dihydroxy-16α-methyl-1,4-pregnadien-3,20-dione.

The present invention refers to a new process for the preparation of mometasone furoate carried out by esterifiication of the 17 hydroxy group of mometasone without prior protection of the 11 hydroxy group.

A great number of clinically useful steroids in which the 17 hydroxy group is esterified and in which the 11 hydroxy group exists in the free form are well known as clinically useful corticosteroids. Typically, the 17 ester function is introduced whilst no other hydroxyl group is present in the molecule, other free hydroxl groups being formed or unmasked later in the synthesis. When other hydroxyl groups, such as an 11 hydroxy function, are present indirect methods are used. It is possible to introduce the 17 ester group by hydrolysis of the 17,21-orthoesters or by carrying out the esterification after protection of the other hydroxyl groups in the molecule. For example, protecting a 11-hydroxy function as a trihaloacetate ester, as a trialkyl-silyl ether or masked as a 9,11 epoxide have all been used to accomplish this.

Surprisingly it has been discovered in the present process that the 17 hydroxy group may be esterified without recourse to protection of the 11 hydroxy group or a masked 11 hydroxy group. In the prior art the introduction of the 17 furoate function has always been carried out with a 9,11 epoxide function present in the molecule which is later converted to the desired 9α-chloro,11β-hydroxy derivative. Mometasone itself can be prepared by different methods as described in the prior art.

It has now been surprisingly found that when mometasone is reacted with 2-furoyl chloride in the presence of a tertiary amine in an inert solvent, mometasone 17-(2-furoate) is obtained in good yield. The 2-furoyl chloride should be used in excess, between 2.5 and 4 mole equivalents being preferred but quantities without this range are also acceptable. There is no limitations concerning the nature of the tertiary amine, whose function is to activate the 2-furoyl chloride and to neutralise the hydrochloric acid liberated during the reaction, although triethylamine is preferred. The tertiary base is used in an excess of 3 to 6 molar equivalents but more or less than these quantities can be used. The solvent is preferably a non polar, water inmiscible solvent and should be such that all the components of the reaction mixture, especially any activated form of the acylating agent, are maintained in solution during the reaction. Dichloromethane has been found to be a suitable solvent although others which meet the above criteria can be used. The reaction is carried out at low to moderate temperatures, typically 0 to 25° C., during several hours, although higher or lower temperatures can be used which may either shorten or extend the reaction time accordingly. When the reaction is carried out in dichloromethane at 10° C. and using triethylamine the reaction is typically complete within 10 to 15 hours.

During the reaction side products, such as the enol furoates at positions 3 and 20, may be formed. This is in no way detrimental to either the yield or the purity of the final product as these compounds are easily converted to mometasone furoate by a short treatment with dilute aqueous hydrochloric acid. Typically, after esterification is complete the reaction solution is treated with aqueous hydrochloric acid during several hours, after removal of excess base by a brief acid wash, to convert these side products to the desired mometasone furoate. This treatment can be carried out in a two phases system at a temperature of 10 to 25° C. although other temperatures may be used. In order to reduce reaction times intimate mixing and the use of a large volume of aqueous hydrochloric acid is preferred to ensure that a large surface area of the two phases are in contact. Alternatively, an organic solvent which is both miscible with water and the solvent of the reaction can be added to increase the concentration of the hydrochloric acid in the organic phase. For example, either ethanol or acetic acid can be used in the proportion 0.5 to 2 volumes for this purpose, in which case the reaction time at 25° C. is typically 3 to 5 hours.

The mometasone furoate can be isolated by standard procedures. Aqueous washes serve to remove water soluble materials, thereafter the dichloromethane is replaced by a lower molecular weight alcohol, such as methanol or ethanol, from which the product crystallises in a pure form and high yield. Further recrystallisations can be carried out from a number of solvents adequate for the purification of pharmaceutical products, such as acetone, methanol and ethanol.

The following Example illustrates but do not in any way limit the present invention:

EXAMPLE 1

Preparation of mometasone 17-(2-furoate)

Mometasone (30 g) was suspended in methylene chloride (300 ml) and the resulting suspension was cooled to 0° C. to 5° C. At this temperature triethylamine (57 ml) was added. 2-Furoyl chloride (24 ml) was then added slowly at a temperature of 5° C. to 10° C. The mixture was then stirred at 8° C. to 12° C. until the level of mometasone present was lower than 0.2% by HPLC. The reaction solution was then cooled to between −5° C. and 5° C. and water (120 ml) was added with stirring. After stirring for 1 hour at 10° C. to 15° C. the mixture was cooled to between 0° C. and 5° C. and concentrated hydrochloric acid was added to adjust the pH of the aqueous layer between 1 and 2.

The phases were separated and the aqueous layer was extracted with methylene chloride (60 ml). To the combined organic layers concentrated hydrochloric acid (90 ml) and acetic acid (30 ml) was added at a temperature between 15° C. and 25° C. Then the two phase reaction mixture was stirred at 20° C. to 25° C. until less than 0.1% of the side products remained as monitored by HPLC. The reaction mixture was cooled to 0° C. to 5° C. and water (120 ml) was added. The lower organic layer was separated, water (120 ml) and 8N aqueous sodium hydroxide solution (about 30 ml) were added to adjust the pH to between 5 and 6. After stirring for 2 hours the organic layer was separated and washed with water (120 ml).

The organic solution [containing the mometasone 17-(2-furoate)] was concentrated by distillation to a volume of 120 ml. Further methanol (120 ml) was added and the mixture was concentrated to 120 ml. This procedure was repeated twice more. The reaction mixture was slowly cooled to between 20° C. and 25° C. and then cooled to between 0° C. and 5° C. and stirred for 2 hours. The crude mometasone 17-(2-furoate) was then filtered off and washed with cold methanol (0° to 5° C., 2×24 ml).

Purification of mometasone 17-(2-furoate)

The wet cake was dissolved in acetone (395 ml) and charcoal (3 g) was added. After stirring at 15° C. to 25° C. for at least 24 hours, the charcoal was filtered off and washed with acetone (90 ml). Charcoal (3 g) was added to the solution and the solution stirred for at least 24 hours at between 15° C. and 25° C. The charcoal was then filtered off and washed with acetone (75 ml).

The solution was concentrated by distillation to a volume of 120 ml. During this concentration the mometasone 17-(2-furoate) started to crystallise. Methanol (120 ml) was added and the solution was again concentrated to 120 ml. This procedure was repeated twice.

The suspension was cooled slowly to between 20° C. and 25° C. and then cooled to between 0° C. and 5° C. and stirred for about 2 hours at this temperature. The pure mometasone 17-(2-furoate) was then filtered off and washed with cold methanol (0° C. to 5° C., 2×24 ml). The product was dried at 60° C. to 70° C. A yield of 29.92 g was obtained.

What is claimed is:

1. A process for the preparation of mometasone furoate by reacting mometasone with 2-furoyl chloride in the presence of a tertiary amine in an inert solvent, by direct esterification of 17 hydroxy group without prior protection of the free 11 hydroxy furoate group.

2. A process according to claim 1, wherein the tertiary amine is triethylamine.

3. A process according to claim 1, wherein the solvent is a non-polar water immiscible solvent such that any activated form of the 2-furoyl chloride is maintained in solution during the reaction.

4. A process according to claim 1 wherein the inert solvent is dichloromethane.

5. A process according to claim 1 wherein 2.5 to 4 molar equivalents of 2-furoyl chloride per molar equivalent of mometasone are used.

6. A process according to claim 1 wherein 3 to 6 molar equivalents of triethylamine per molar equivalent of mometasone are used.

7. A process according to claim 1 wherein the reaction is carried out at a temperature from 0° C. to 25° C.

8. A process according to claim 1, further comprising treating the products of the reaction with aqueous hydrochloric acid to remove enol furoates formed at positions 3 and 20 of the mometasone furoate.

* * * * *